US00PP34636P2

(12) United States Plant Patent
Fouillet

(10) Patent No.: US PP34,636 P2
(45) Date of Patent: Oct. 11, 2022

(54) APPLE TREE NAMED 'CANOPY'

(50) Latin Name: *Malus domestica*
Varietal Denomination: 'Canopy'

(71) Applicant: IFO S.A.R.L., Seiches-sur-le-Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 0 days.

(21) Appl. No.: 17/803,055

(22) Filed: Jan. 25, 2022

(30) Foreign Application Priority Data

Jul. 9, 2021 (FR) ..... 21175

(51) Int. Cl.
*A01H 5/08* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./172
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Canopy' is a new apple tree notable for its attractive yellow-green fruit, which stores well and is well-suited for the fresh market.

6 Drawing Sheets

Latin name: *Malus domestica.*
Variety denomination: 'Canopy'.

BACKGROUND OF THE VARIETY

'Canopy' is a new and distinct variety of apple tree (*Malus domestica*) obtained from a controlled cross of female parent 'Co-op 38' (U.S. Plant Pat. No. 9,392, expired) x 'Dalivair' (male parent, not patented) carried out at Seiches-sur-le-Loir, France in 2004. Seeds obtained from the cross were planted at Seiches-sur-le-Loir, and 'Canopy' was selected from the resulting seedlings for propagation and further observation. 'Canopy' was first asexually propagated by grafting at Seiches-sur-le-Loir in 2012, and has since been observed to remain true to type through successive asexually propagated generations.

BRIEF DESCRIPTION OF THE VARIETY

The 'Canopy' apple tree is distinguished by its attractive yellow-green fruit, which is well-suited for fresh consumption. Comparisons of 'Canopy' to its parents and to similar variety 'Smeralda' (U.S. Plant Pat. No. 24,137) are shown in Tables 1, 2 and 3 below.

TABLE 1

Comparison of 'Canopy' to Female Parent 'Co-op 38'

| Characteristic | 'Canopy' | 'Co-op 38' |
|---|---|---|
| Petal length | 17.6 mm | 14.0 mm |
| Tree habit | Drooping | Semi-upright |
| Leaf apex | right angle with broad short to long acuminate | Acute to acuminate |

TABLE 1-continued

Comparison of 'Canopy' to Female Parent 'Co-op 38'

| Characteristic | 'Canopy' | 'Co-op 38' |
|---|---|---|
| Harvest date | 16 days after 'Golden Delicious'(2020) | 40 to 60 days after 'Golden Delicious' |
| Trunk lenticel size | 2 mm × 1 mm | 7 mm × 4 mm |

TABLE 2

Comparison of 'Canopy' to Male Parent 'Dalivair'

| Characteristic | 'Canopy' | 'Dalivair' |
|---|---|---|
| Lenticel russet | Present | Absent |
| Intensity and frequency of greyed-red overcolor | Less than 'Dalivair' | More than 'Canopy' |
| Flavor | Sweeter than 'Dalivair' | Less sweet than 'Canopy' |
| Date of full bloom | Earlier (April 13) | Later (April 16) |
| Maturity as measured by starch level (Oct. 19, 2021) | 6/10 | 5/10 |

TABLE 3

Comparison of 'Canopy' to Similar Variety 'Smeralda'

| Characteristic | 'Canopy' | 'Smeralda' |
|---|---|---|
| Trunk color | Greyed-purple N187D over greyed-orange 166B | Greyed-green 197A |
| Leaf attitude in relation to shoot | Upward | Outward |
| Diameter of fully open flower | 39.3 mm | 35 mm |
| Length of stalk | 16.6 mm | 25.8 mm |
| Flesh color | Yellow-green 149D | Yellow 4D |

BRIEF DESCRIPTION OF THE PHOTOGRAPHS

The accompanying photographs were obtained in 2021 at Seiches-sur-le-Loir, France. The trees depicted were planted in 2018.

DETAILED BOTANICAL DESCRIPTION OF THE VARIETY

Figure 1:
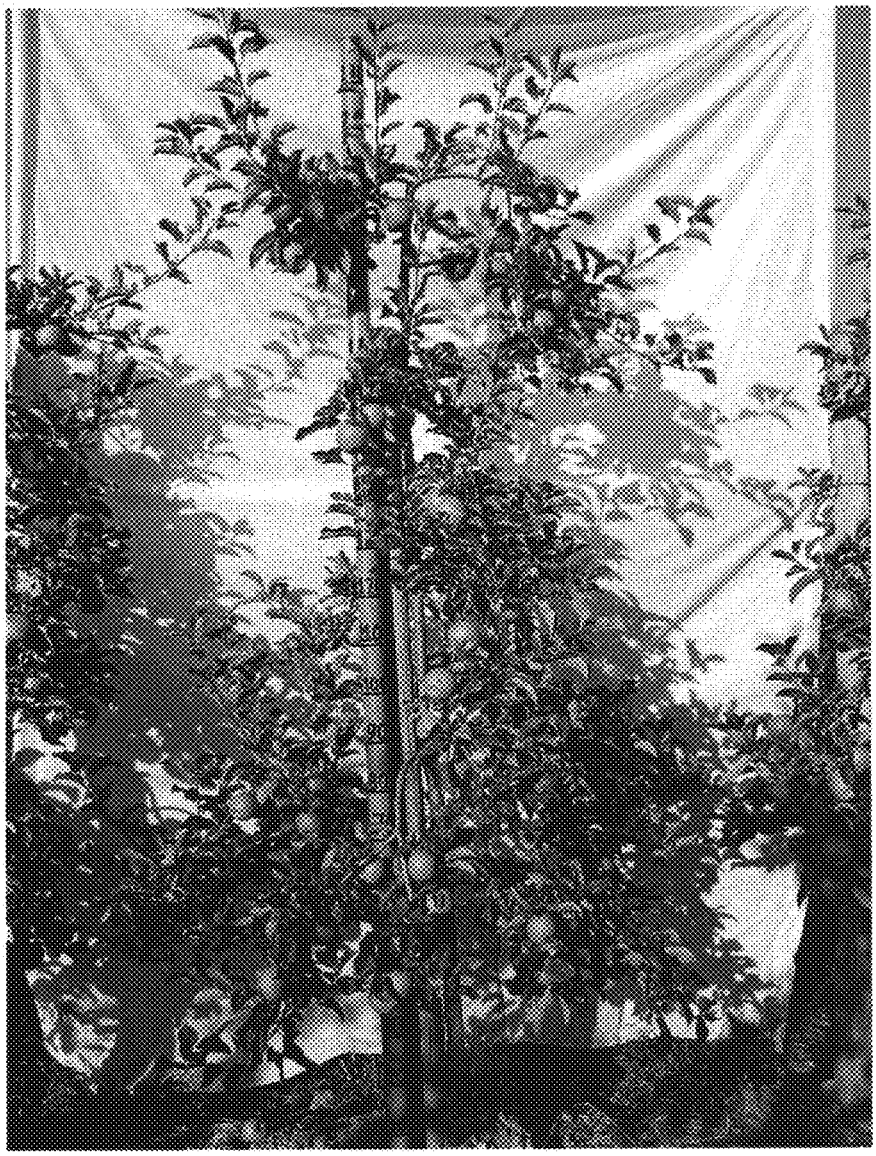
FIG. 1 is a photograph of a 'Canopy' apple tree with leaves and fruit.
Figure 2:
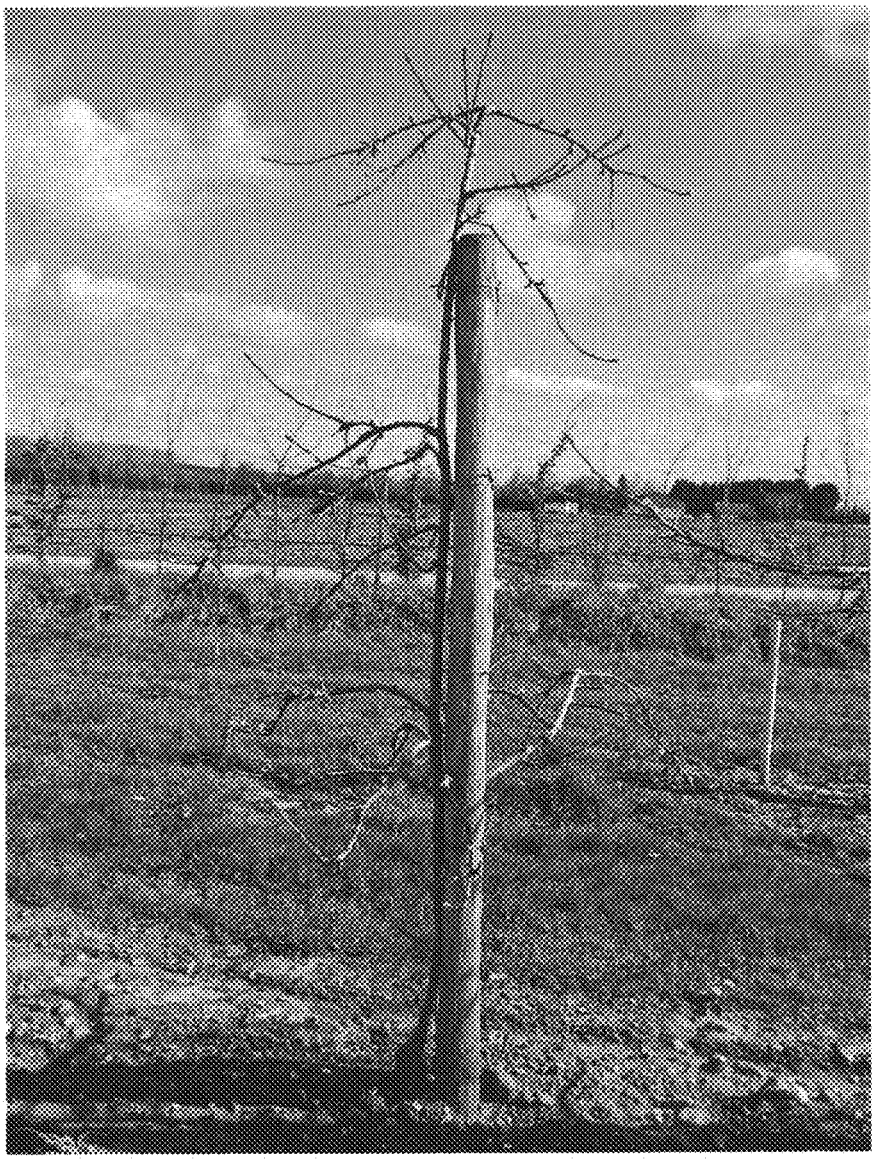
FIG. 2 is a photograph of a 'Canopy' apple tree without leaves or fruit.
Figure 3:
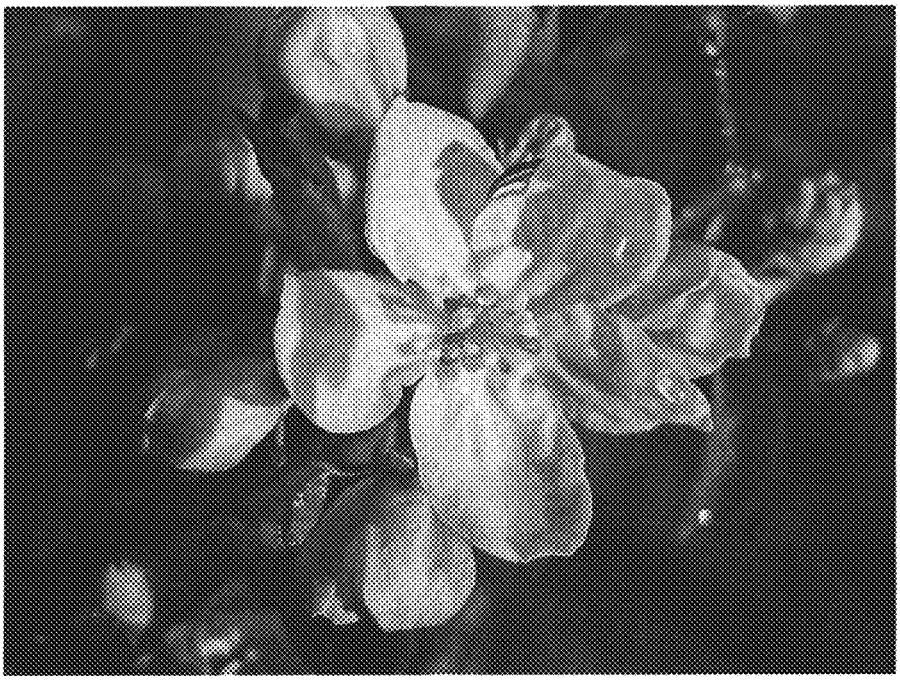
FIG. 3 is a photograph of a blossom and flower buds on a 'Canopy' apple tree.
Figure 4:
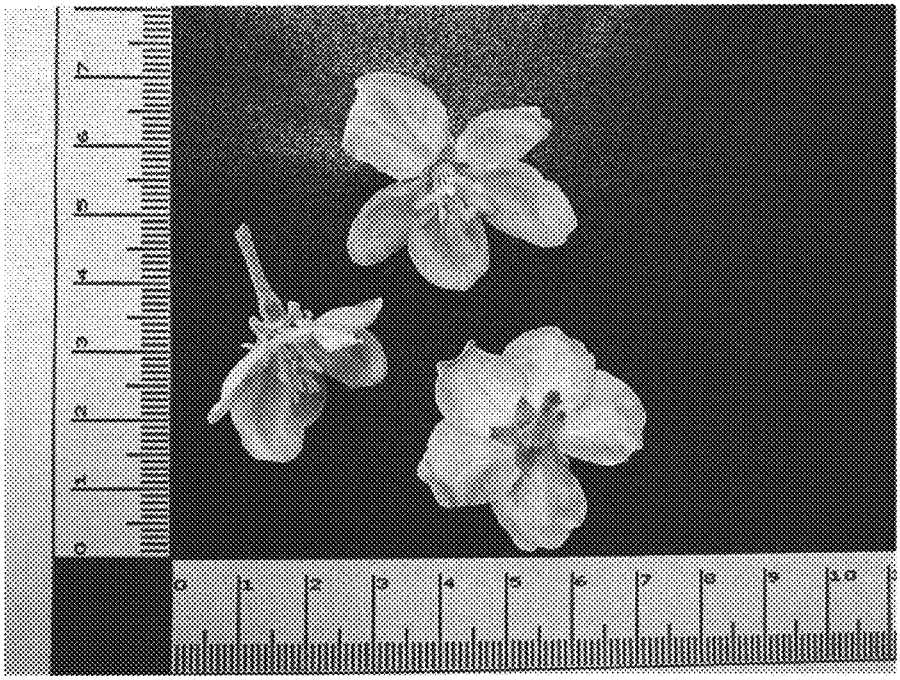
FIG. 4 is a photograph of blossoms from a 'Canopy' apple tree.
Figure 5:
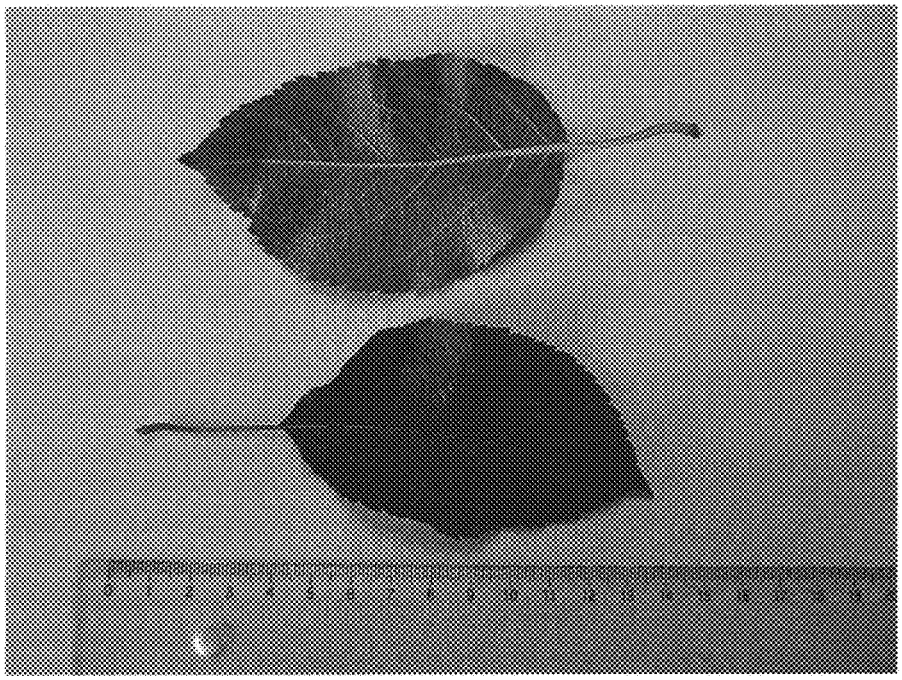
FIG. 5 is a photograph of leaves from a 'Canopy' apple tree.
Figure 6:
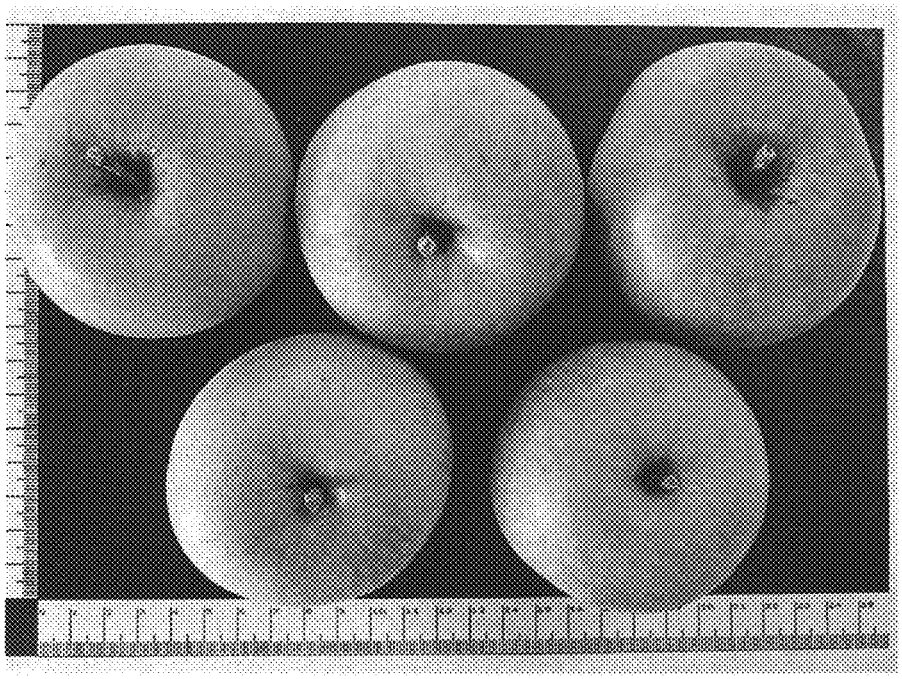
FIG. 6 is a photograph of a stem-end view of apples from a 'Canopy' apple tree.
Figure 7:
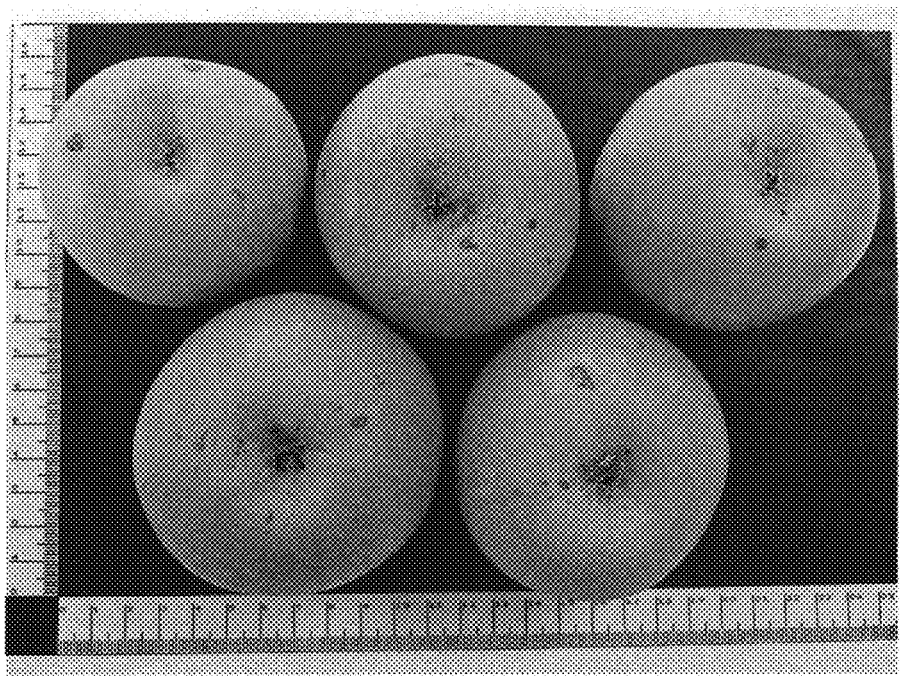
FIG. 7 is a photograph of a calyx-end view of apples from a 'Canopy' apple tree.
Figure 8:
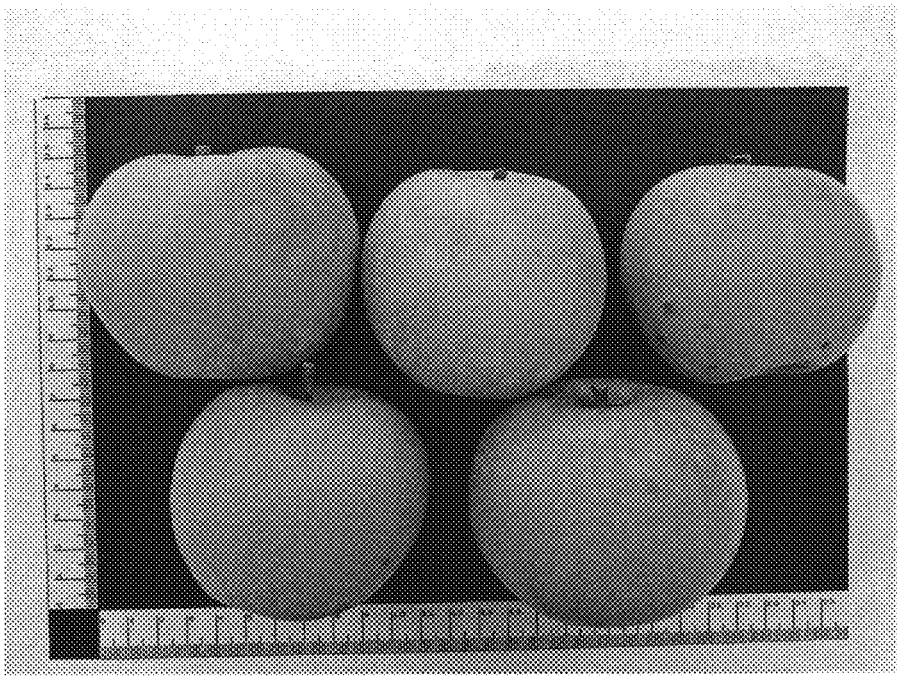
FIG. 8 is a photograph of a side view of apples from a 'Canopy' apple tree.
Figure 9:
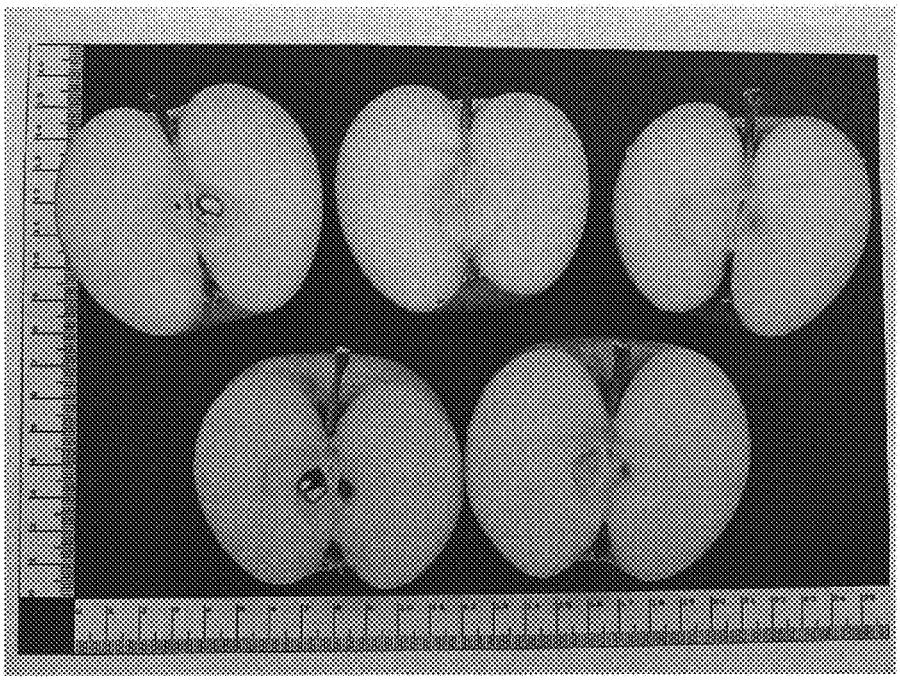
FIG. 9 is a photograph of sectioned apples from a 'Canopy' apple tree.
Figure 10:
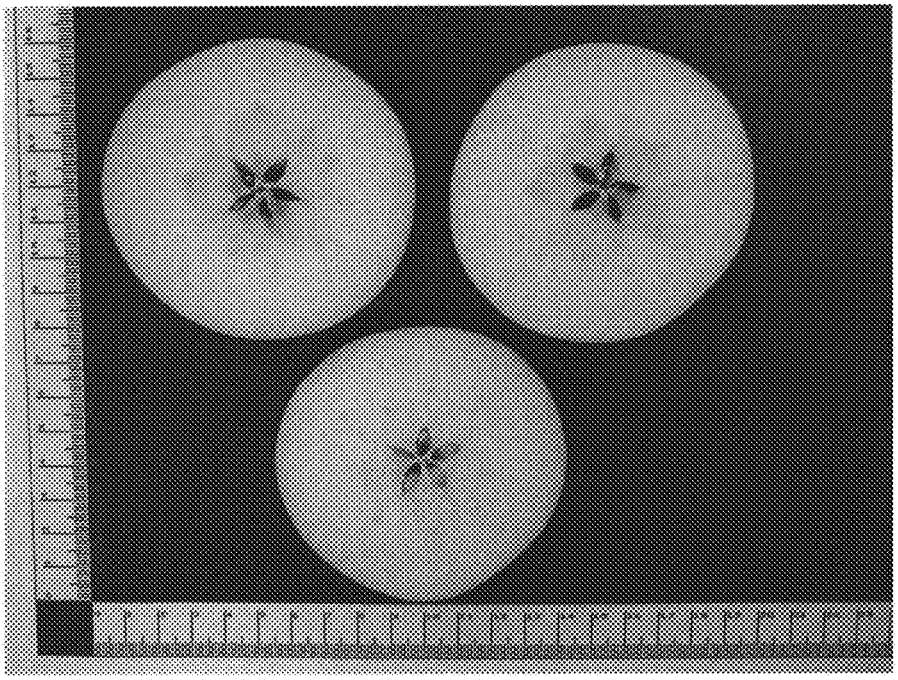
FIG. 10 is a photograph of sectioned apples from a 'Canopy' apple tree.

The following detailed botanical description was recorded at Seiches-sur-le-Loir, France during the 2021 growing season (unless otherwise noted). The described trees were planted in 2018 and grown on Pajam®2 'Cepiland' (U.S. Plant Pat. No. 7,715) rootstock. All colors are described with reference to The Royal Horticultural Society Colour Chart ($6^{th}$ ed. 2015, reprinted 2019). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor.*—Medium to high.
- *Type.*—Ramified.
- *Habit.*—Drooping.
- *Bearing.*—On shoots and spurs.
- *Spread of mature tree.*—1.4 meters.
- *Height.*—2.2 m.
- *Trunk diameter* (*at* 30 *cm above the graft*).—44.2 mm.
- *Bark texture.*—Smooth with prominent lenticels.
- *Bark color.*—Greyed-purple N187D over greyed-orange 166B.
- *Lenticel length.*—2 mm.
- *Lenticel width.*—1 mm.
- *Lenticel height.*—0.7 mm.
- *Lenticel shape.*—Slightly elongated ovate.
- *Lenticel color.*—Orange-white 159C.
- *Lenticel density.*—Dense.

Branch (fruiting branches located at around 1 m above the graft union):
- *Length.*—70 cm.
- *Diameter.*—14.6 mm.
- *Crotch angle.*—80°.
- *Bark color.*—Greyed-orange 166B and greyed-purple N187D.
- *Lenticel length.*—1.5 mm.
- *Lenticel width.*—0.8 mm.
- *Lenticel height.*—0.3 mm.
- *Lenticel shape.*—Slightly elongated ovate.
- *Lenticel color.*—Orange-white 159C.
- *Lenticel density.*—Medium to dense, about 5 per $cm^2$.
- *Color of vegetative buds.*—Greyed-purple 187A.
- *Shape of vegetative bud apex.*—Acute.
- *Position of vegetative buds in relation to shoots.*—Adpressed.

One year old shoot:
- *Length.*—24.8 cm.
- *Diameter.*—3.8 mm.
- *Growth pattern.*—Straight.
- *Color.*—Greyed-brown N199B.
- *Pubescence.*—Moderate.
- *Internode length.*—27.7 mm.
- *Lenticel length.*—0.8 mm.
- *Lenticel width.*—0.5 mm.
- *Lenticel heigh.*—0.1 mm.
- *Lenticel shape.*—Round to slightly elongated ovate.
- *Lenticel color.*—Yellow-white 158D.
- *Lenticel density.*—Dense, about 10 per $cm^2$.

Flower buds:
- *Stage described.*—Bud burst.
- *Quantity per spur.*—10.
- *Bud shape.*—Medium ovate.
- *Apex shape.*—Slightly acute.
- *Length.*—13.2 mm.
- *Diameter.*—7.5 mm.
- *Color.*—Yellow-green 147D.

Flowers:
- *Inflorescence type.*—Umbel.
- *Diameter of fully open flower.*—39.3 mm.
- *Depth of fully open flower.*—9.4 mm.
- *Relative position of petal margin.*—Overlapping.
- *Number per cluster.*—Average 5.3.
- *Fragrance.*—Typical of apple varieties.
- *Date of first bloom.*—April 9.
- *Date of full bloom.*—April 13.
- *Pollination requirement.*—Most varieties with similar bloom date.

Petals:
- *Number per flower.*—5.
- *Petal shape.*—Circular to obovate, slightly elongated.
- *Length.*—17.6 mm.
- *Width.*—14.8 mm.
- *Apex shape.*—Obtuse to rounded.
- *Base shape.*—Rounded.
- *Margin.*—Entire.
- *Color of upper surface.*—White NN155D.
- *Color of lower surface.*—White NN155D.
- *Texture.*—Both surfaces smooth.
- *Color of venation.*—Red-purple 64C.
- *Petal vein prominence.*—Medium.

Pistils:
- *Length.*—12.4 mm.
- *Color.*—Yellow-green 144C.
- *Quantity per flower.*—5.

Stigma:
- *Diameter.*—0.5 mm.
- *Color.*—Greyed-orange N167B.
- *Position of stigma relative to anther.*—Above.

Style:
*Length.*—8.2 mm.
*Color.*—Yellow-green 144C.
Ovary:
*Length.*—3.2 mm.
*Diameter.*—1.3 mm.
*Color.*—Yellow-green 145C.
Stamens:
*Quantity.*—Average 19.6.
*Length of filament.*—8 mm.
*Color of anther.*—Yellow 8C.
*Pollen presence.*—Present in moderate quantity.
*Pollen color.*—Yellow 7D.
Pedicel:
*Length.*—16.1 mm.
*Diameter.*—1.5 mm.
*Color.*—Green 143C.
*Pubescence.*—Moderate.
Sepals:
*Quantity.*—5.
*Color of upper surface.*—Green 144B with red-purple 64B on tip.
*Color of lower surface.*—Green 144B with red-purple 64B on tip.
*Sepal shape.*—Slightly elongated triangular.
*Apex shape.*—Strongly acute.
*Margin (smooth, serrated, etc.).*—Entire.
*Pubescence.*—Moderate to high.
*Attitude in relation to corolla.*—Downward.
Leaves:
*Shape.*—Slightly elongated ovate.
*Length.*—9.4 cm.
*Width.*—5.5 cm.
*Blade margin.*—Serrate.
*Undulation of blade margin.*—Moderate.
*Apex.*—Right angle with broad, short to long acuminate tip.
*Base shape.*—Broad wedge-shaped, convex.
*Leaf color-upper surface.*—Green 139A, primary vein yellow-green 144C.
*Leaf color-lower surface.*—Green 138B, primary vein yellow green 144C.
*Pubescence.*—None on upper surface; weak to medium on lower surface.
*Attitude in relation to shoot.*—Upward.
*Arrangement.*—Alternate.
Petiole:
*Length.*—3.2 cm.
*Diameter.*—1.8 mm.
*Color.*—Yellow-green 144C.
Stipules:
*Shape.*—Oblanceolate.
*Length.*—3.9 mm.
*Widt.*—0.4 mm.
*Color.*—Green 143A.
Fruit:
*Quantity per cluster.*—5.
*Diameter.*—74 mm.
*Height.*—62 mm.
*Height to width.*—0.84.
*Weight.*—187 g.
*General shape in profile.*—Conic with flat tapering sides on apical half.
*Position of maximum diameter.*—At equator.
*Ribbing.*—Weak.
*Crowning at calyx end.*—Weak.
*Bloom of skin.*—Absent.
*Greasiness of skin.*—Absent.
*Amount of anthocyanin over-color on young fruit.*—About 30%.
*Background color of skin.*—Yellow-green 145C.
*Over color of skin.*—Yellow-green 144B; greyed-red 178C over 20% of surface on some fruits.
*Amount of over color.*—95%.
*Intensity of over color.*—Intense.
*Pattern of over color.*—Flushed and mottled.
*Fruit lenticel color.*—Yellow-green 145C, with a point of russet in the center of each lenticel.
*Fruit lenticel diameter.*—0.3 mm.
*Fruit lenticel shape.*—Round near calyx end; increasingly elongated nearing stalk end.
*Fruit lenticel quantity.*—Many.
*Russet around stalk cavity.*—Weak.
*Russet on cheeks.*—In center of lenticels only.
*Area of russet around eye basin.*—Very weak.
*Length of stalk.*—16.6 mm.
*Diameter of stalk.*—2.6 mm.
*Stalk color.*—Greyed-brown N199D.
*Depth of stalk cavity.*—16 mm.
*Width of stalk cavity.*—33 mm.
*Depth of eye basin.*—8.9 mm.
*Width of eye basin.*—31 mm.
*Diameter of eye.*—7.3 mm.
*Aperture of eye.*—Closed to slightly open.
*Length of sepal.*—4.6 mm.
*Firmness of flesh.*—Medium, 8.77 kg/cm at harvest (2021).
*Flesh texture.*—Medium, neither fine nor coarse.
*Number of locules.*—5.
*Aperture of locules.*—Moderately open.
*Locule length.*—0.86 mm.
*Locule width.*—0.36 mm.
*Flavor.*—Slightly acidic.
*Juiciness.*—Moderate.
*Brix.*—13° Brix.
*Flesh color.*—Yellow-green 149D.
Seeds:
*Quantity per fruit.*—Average 7.2.
*Length.*—7.6 mm.
*Width.*—4.9 mm.
*Shape.*—Slightly elongated ovate.
*Color.*—Greyed-orange 165A.
Harvest:
*Harvest date.*—October 3 (2020); 16 days after 'Golden Delicious' (not patented).
*Number of picks.*—1 or 2.
Disease resistance/susceptibility: Resistant to apple scab.
Eating quality: Good.
Storageability: Medium to long.
Market use: Fresh consumption.

What is claimed is:

1. A new and distinct apple tree named 'Canopy' substantially as described and illustrated herein.

* * * * *